(12) United States Patent
Roby et al.

(10) Patent No.: US 10,285,816 B2
(45) Date of Patent: May 14, 2019

(54) IMPLANT INCLUDING CARTILAGE PLUG AND POROUS METAL (71) Applicant: Zimmer, Inc., Warsaw, IN (US)

(72) Inventors: Keith A. Roby, Jersey City, NJ (US);
Bradford J. Coale, Chester, NJ (US);
John Chernosky, Brick, NJ (US)

(73) Assignee: Zimmer, Inc., Warsaw, IN (US)

( * ) Notice: Subject to any disclaimer, the term of this patent is extended or adjusted under 35 U.S.C. 154(b) by 149 days.

(21) Appl. No.: 14/956,974

(22) Filed: Dec. 2, 2015

(65) Prior Publication Data

US 2016/0206432 A1    Jul. 21, 2016

Related U.S. Application Data

(60) Provisional application No. 62/105,828, filed on Jan. 21, 2015.

(51) Int. Cl.
*A61F 2/30* (2006.01)

(52) U.S. Cl.
CPC ............ *A61F 2/30756* (2013.01); *A61F 2/30* (2013.01); *A61F 2002/305* (2013.01); *A61F 2002/30011* (2013.01); *A61F 2002/30014* (2013.01); *A61F 2002/30029* (2013.01); *A61F 2002/3037* (2013.01); *A61F 2002/3092* (2013.01); *A61F 2002/3098* (2013.01); *A61F 2002/30224* (2013.01); *A61F 2002/30329* (2013.01); *A61F 2002/30331* (2013.01); *A61F 2002/30362* (2013.01); *A61F 2002/30518* (2013.01); *A61F 2002/30576* (2013.01); *A61F 2002/30761* (2013.01); *A61F 2002/30968* (2013.01); *A61F 2002/30985* (2013.01); *A61F 2210/0076* (2013.01); *A61F 2310/00023* (2013.01); *A61F 2310/00029* (2013.01); *A61F 2310/00131* (2013.01); *A61F 2310/00341* (2013.01)

(58) Field of Classification Search
CPC .. A61F 2002/30751; A61F 2002/30011; A61F 2002/30028–2002/30029; A61F 2002/30329–2002/30528; A61F 2/30756–2002/30766; A61F 2/30766
See application file for complete search history.

(56) References Cited

U.S. PATENT DOCUMENTS 5,282,861 A     2/1994  Kaplan
8,556,972 B2 * 10/2013  Gordon .................... A61F 2/28
                                                 623/16.11
(Continued)

OTHER PUBLICATIONS

Levine, Brett R, et al., "Experimental and clinical performance of porous tantalum in orthopedic surgery", Biomaterials, (27), (Sep. 2006), 4671-81.

*Primary Examiner* — Thomas Sweet
*Assistant Examiner* — Rebecca S Preston
(74) *Attorney, Agent, or Firm* — Schwegman Lundberg & Woessner, P.A.

(57) ABSTRACT

An implant and methods for use in various procedures are disclosed. According to an example of the present application, an orthopedic implant is disclosed. The implant can include a base and a body. The base can comprise a porous metal material configured to encourage bone ingrowth into the base. The body can be coupled to the base and can comprise a second material that differs from the porous metal material of the base.

15 Claims, 7 Drawing Sheets

(56) References Cited

U.S. PATENT DOCUMENTS

| | | | |
|---|---|---|---|
| 2003/0220700 A1* | 11/2003 | Hammer | A61B 17/0642 623/23.58 |
| 2007/0100463 A1* | 5/2007 | Aram | A61F 2/3868 623/20.29 |
| 2008/0195221 A1* | 8/2008 | Howald | A61B 17/1635 623/22.32 |
| 2009/0319045 A1* | 12/2009 | Truncale | A61F 2/28 623/16.11 |
| 2012/0046752 A1* | 2/2012 | Blanchard | A61F 2/30756 623/18.11 |

* cited by examiner

IMPLANT INCLUDING CARTILAGE PLUG AND POROUS METAL

CLAIM OF PRIORITY

This application claims the benefit of U.S. Provisional Patent Application Ser. No. 62/105,828, filed on Jan. 21, 2015, the benefit of priority of which is claimed hereby, and which is incorporated by reference herein in its entirety.

TECHNICAL FIELD

The present application relates to orthopedic prostheses, and more particularly, to porous implants and methods of using the same.

BACKGROUND

Orthopedic procedures are commonly utilized to repair and/or replace damaged tissue in the human body. Such procedures can utilize orthopedic implants to replace or augment body components or portions of body components that cannot be regenerated or are no longer functioning properly. Examples of orthopedic implants include spinal implants, dental implants, artificial knees, hips, and ankle joints.

Some orthopedic implants and/or procedures can utilize biocompatible materials to: provide structural support to an orthopedic implant, fill voids in bone, reconstruct or repair joints, or provide a structure for permitting ingrowth and attachment of tissue.

OVERVIEW

The present inventors recognize, among other things, an opportunity to improve upon the structural stability, and ultimately the regenerative ability of implants, in particular, cartilage implants. Thus, the present inventors propose an implant that can have a base that comprises a first material (e.g., a porous metal) and a body that comprises a second material, which can differ from the first material. The body can be configured to fill a void in cartilage and can be configured to promote cartilage ingrowth. Similarly, the base can be configured to fill a void in bone and can be configured to promote bone ingrowth to aid in implant fixation. Fixation of the base to the bone can provide structural stability for the body, and thereby, aid in facilitating cartilage ingrowth into the body.

According to an example of how the implant can be used, if a physician discovers a void (as a result of a defect, wear, tear, etc.) in cartilage, an aperture can be formed in the bone underlying the cartilage void and the implant can be inserted therein. The aperture and implant can be configured such that the base can be disposed adjacent the bone while the body can be disposed adjacent cartilage. Thus, the implant (specifically, the body) can be used as a "plug" to fill the cartilage void, thereby allowing the body to interface with adjacent cartilage and act as cartilage scaffold to promote cartilage ingrowth. The implant described herein can be used in any location in the human body having a cartilage void that is desirable to repair. An example of a possible location includes human joints (e.g., knee, hip, ankle, spine, etc.).

To further illustrate the implant and methods disclosed herein, a non-limiting list of examples is provided here:

In Example 1, an orthopedic implant can comprise a base and a body. The base can comprise a porous metal material configured to encourage bone ingrowth into the base. The body can be coupled to the base and comprising a second material that differs from the porous metal material of the base, wherein the body is configured to encourage cartilage ingrowth into the body.

In Example 2, the implant of Example 1, wherein the porosity of the porous metal material can be between 55% and 90%.

In Example 3, the implant of any one or any combination of Examples 1 to 2, wherein second material can a porous material that comprises at least one of a polymeric material and a coral.

In Example 4, the implant of any one or any combination of Examples 1 to 3, wherein the polymeric material can comprise a biocompatible polymer that includes at least one of polycaprolactone, poly(lactic acid), poly(glycolic acid), copolymers of lactic acid and glycolic acid, poly(ethylene glycol), and combinations thereof.

In Example 5, the implant of any one or any combination of Examples 1 to 4, wherein the body can be coupled to the base by one or more mechanical features that include at least one of a fastener, a hook, a detent, a feature, a plug, a male/female connection, an adhesive, and combinations thereof.

In Example 6, the implant of any one or any combination of Examples 1 to 5, wherein the body can comprise a core having a first porosity and an outer shell surrounding as least a portion of the core and having a second porosity that differs from the first porosity.

In Example 7, the implant of any one or any combination of Examples 1 to 6, wherein the second porosity of the outer shell can be substantially similar to a porosity of cartilage, and wherein the first porosity of the core can be higher than the second porosity of the outer shell.

In Example 8, the implant of any one or any combination of Examples 1 to 7, wherein the core can be coupled to the base and the shell can surround at least a portion of the core that opposes and is spaced from the base.

In Example 9, the implant of any one or any combination of Examples 1 to 8, wherein the base can comprise a tantalum or tantalum alloy.

In Example 10, a method of treating a cartilage void within a patient, the method can comprise removing at least a portion of bone underlying the cartilage void to a desired depth to create an aperture within the bone, and positioning an implant having a base comprising a porous metal material and a body comprising a second porous material within the aperture such that the base is disposed adjacent the bone and the body is disposed adjacent cartilage of the patient.

In Example 11, the method of Example 10, wherein positioning the implant can configure the body as a cartilage scaffold and the base as a bone scaffold.

In Example 12, the method of any one or any combination of Examples 10 to 11, wherein the porosity of the porous metal material can be between 55% and 90%.

In Example 13, the method of any one or any combination of Examples 10 to 12, wherein the porous metal material can comprise a tantalum or tantalum alloy.

In Example 14, the method of any one or any combination of Examples 10 to 13, wherein the second porous material differs from the porous metal material and can comprise at least one of a polymeric material and a coral.

In Example 15, an orthopedic implant can comprise a base and a body. The base can comprise a porous metal material having a porosity between 55% and 90% configured to encourage bone ingrowth into the base to facilitate attachment of the base to bone. The body can comprise a polymeric material configured to encourage cartilage ingrowth into the body, wherein the body and the base can be configured to be coupled together by one or more mechanical features.

In Example 16, the implant of Example 15, wherein the polymeric material can comprise a biocompatible polymer that includes at least one of polycaprolactone, poly(lactic acid), poly(glycolic acid), copolymers of lactic acid and glycolic acid, poly(ethylene glycol), and combinations thereof.

In Example 17, the implant of any one or any combination of Examples 15 to 16, wherein the body comprises a core having a first porosity and an outer shell surrounding as least a portion of the core and having a second porosity that differs from the first porosity.

In Example 18, the implant of any one or any combination of Examples 15 to 17, wherein the second porosity of the outer shell is substantially similar to a porosity of cartilage, and wherein the first porosity of the core is higher than the second porosity of the outer shell.

In Example 19, the implant of any one or any combination of Examples 15 to 18, wherein the core is coupled to the base and the shell surrounds at least a portion of the core that opposes and is spaced from the base.

In Example 20, the implant of any one or any combination of Examples 15 to 19, wherein the porous metal material can comprise a tantalum or tantalum alloy.

In Example 21, the implant or method of any one or any combination of Examples 1-20 can optionally be configured such that all elements or options recited are available to use or select from.

These and other examples and features of the present implants and methods will be set forth in part in the following Detailed Description. This Overview is intended to provide non-limiting examples of the present subject matter—it is not intended to provide an exclusive or exhaustive explanation. The Detailed Description below is included to provide further information about the present apparatus, systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to implants and methods for use in various procedures. According to an example, the implant can have a base that comprises a first material (e.g., a porous metal) and a body that comprises a second material. The body can be configured to fill a void in cartilage and can be configured to promote cartilage ingrowth. Similarly, the base can be configured to fill a void in bone and can be configured to promote bone ingrowth to aid in implant fixation. Fixation of the base to bone can provide structural stability for the body, and thereby, aid in cartilage ingrowth into the body.

Figure 1A:
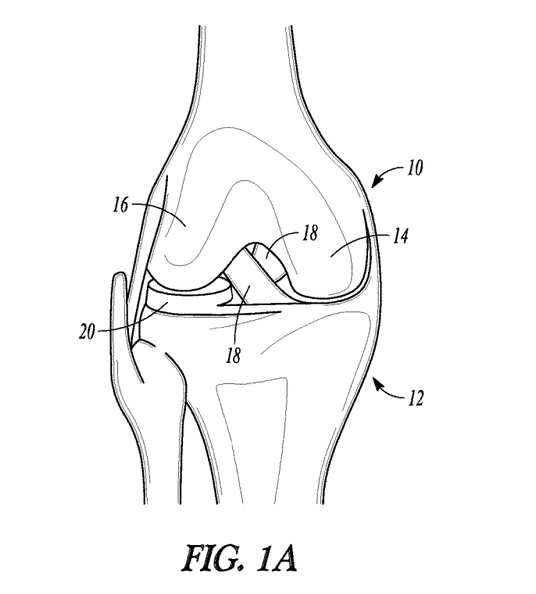
FIG. 1A is an anterior view of a natural femur and tibia.
Figure 1B:
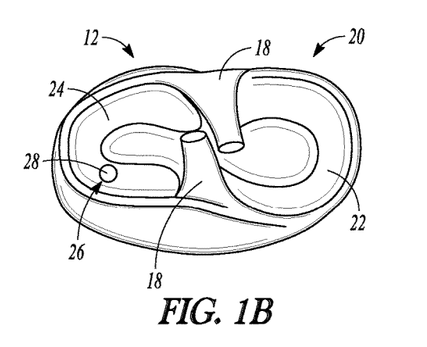
FIG. 1B is a top view of the tibia of FIG. 1A having a cartilage void therein.

FIG. 1A illustrates a distal portion of a natural femur 10 and a proximal portion of a tibia 12. The femur 10 can include medial 14 and lateral 16 condyles at a distal end of the femur 10. Various ligaments 18 can be attached to the femur 10 and/or the tibia 12. Cartilage can reside on the articulation surfaces of any joint, such as the knee joint with tibial cartilage 20 in FIG. 1A. FIG. 1B is a top view of the tibia 12 and further illustrates some of the cartilage 20 including a medial meniscus 22 and a lateral meniscus 24 that are located on the tibia 12 respective to the medial 14 and lateral 16 condyles (FIG. 1A).

Figure 1C:
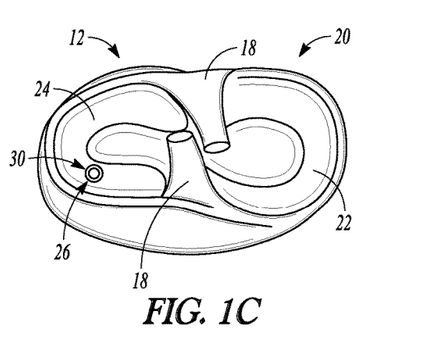
FIG. 1C is a top view of the tibia of FIG. 1B having an implant disposed in the cartilage void.

As illustrated in FIG. 1B, the lateral meniscus 24 contains a cartilage void 26 that can result from a tear, wear, defect, etc. The cartilage void 26 can expose underlying bone 28 of the tibia 12. FIG. 1C illustrates an implant 30 that can be inserted into the cartilage void 26 and underlying bone 28. Thus, the implant 30 can be disposed within the cartilage void 26 to interface with adjacent cartilage 20 (e.g., lateral meniscus 24). In some instances, the implant 30 can abut the adjacent cartilage 20 and/or bone. As will be discussed subsequently, the implant 30 can be configured to encourage bone ingrowth into a first portion thereof and can additionally be configured to encourage cartilage ingrowth into a second portion thereof, in the given example from the lateral meniscus 24.

Figure 2:
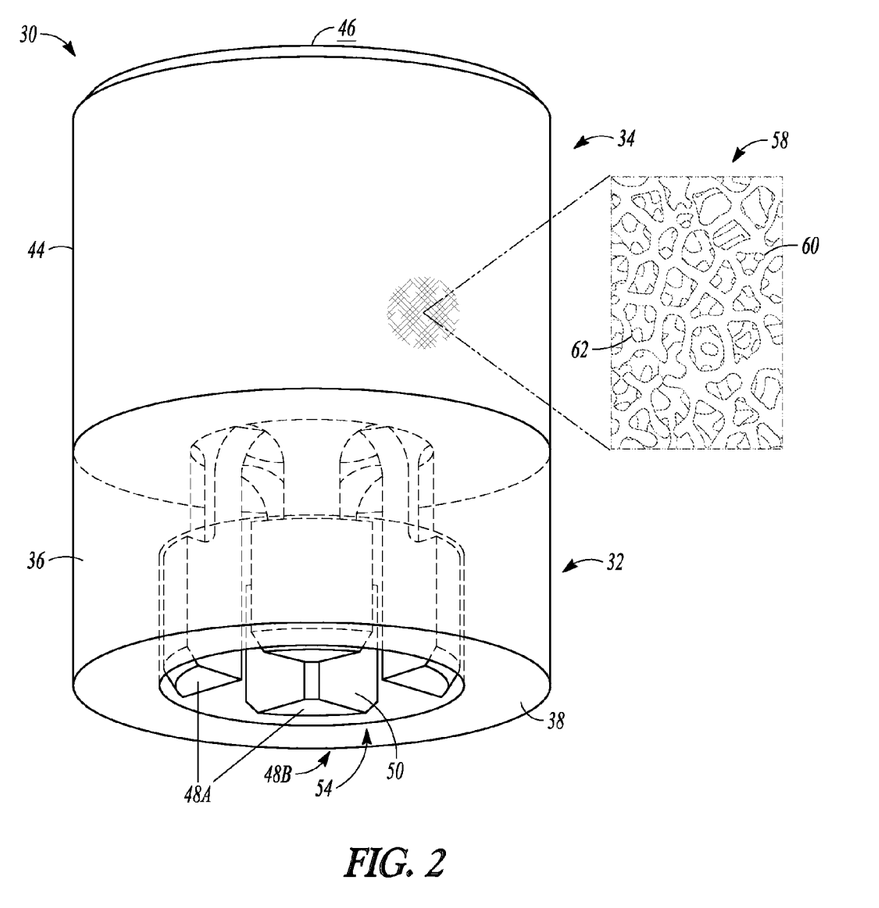
FIG. 2 is a perspective view of an implant including a base and a body, according to an example of the present application.
Figure 2A:
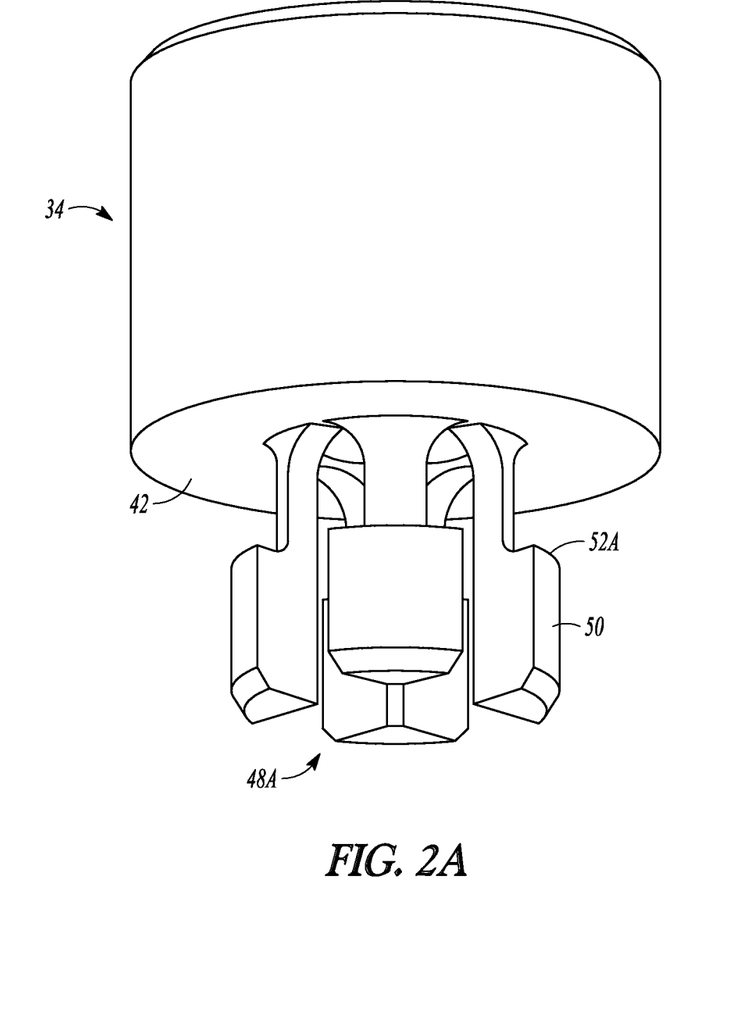
FIG. 2A is a view of the body of the implant of FIG. 2.
Figure 2B:
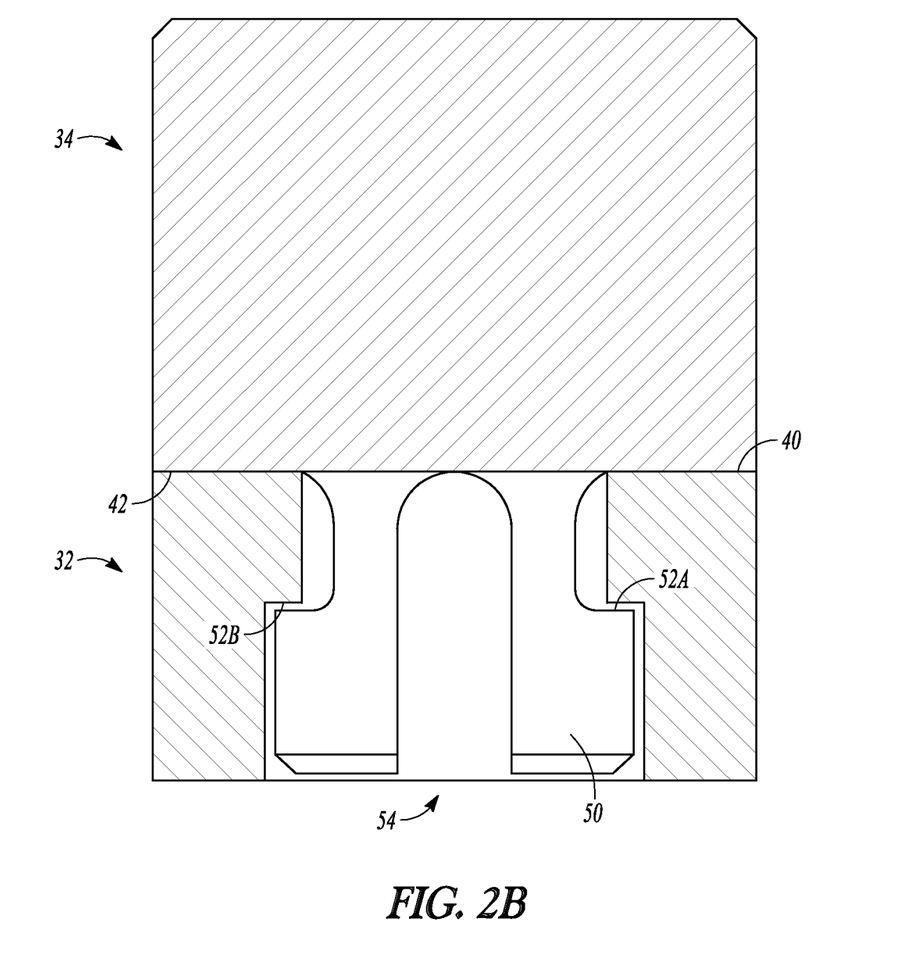
FIG. 2B is a cross-section of the implant of FIG. 2.

FIGS. 2, 2A, and 2B illustrate an exemplary configuration of the implant 30. The implant 30 can include a base 32 and a body 34. In some cases, the base 32 can comprise a porous metal material. The porosity of the porous metal material can be between 55% and 90%. Similarly, the body 34 can comprise a porous material. However, the porous material and structure of the body 34 can differ from the porous metal material of the base 32. The composition of the base 32 and the body 34 will be discussed in further detail subsequently. Although illustrated as having a generally cylindrical shape in FIGS. 2, 2A and 2B, a size (e.g., axial thickness, diameter, etc.) and shape of the implant 30 including the base 32 and the body 34 can be varied from example to example, and can be determined based, in part, on the size and shape of the cartilage void 26 (FIG. 1B), the desired depth of bone removal to achieve sufficient fixation, the procedure being performed, etc., as described below. The size of the base 32 (axial thickness, diameter, etc.) can be selected to provide adequate structural support for the body 34 and may differ in shape and/or size therefrom in some instances. Although base 32 and body 34 are illustrated as entirely comprised porous materials in FIGS. 2, 2A, and 2B, according to further examples parts of the base 32 and/or body 34 can be solid while other parts of the base 32 and/or body 34 can be comprised of porous material(s).

According to the example of FIG. 2, the base 32 can have a side surface 36 and bottom surface 38, as well as a top surface 40 (FIG. 2B) that can be adapted to interface with the body 34. Similarly, the body 34 can have a bottom surface 42 (FIGS. 2A and 2B), side surface 44, and a top surface 46. As shown in FIGS. 2 and 2B, the base 32 can be coupled to the body 34. This can be accomplished by mechanical features 48A and 48B, for example. Although the examples of FIGS. 2-2B illustrate mechanical features 48A (not shown in FIG. 2A) and 48B can be used, in other examples the base 32 can be coupled to the body 34 by other attachment features and techniques, including, but not limited to, adhesion, brazing, welding, molding, bonding, and/or plasma spray. The examples of FIGS. 2-2A illustrate mechanical features 48A and 48B can comprise a male/female connection. Specifically, FIGS. 2-2B illustrate the use of a plug 50 and features 52A and 52B (FIG. 2B) type connection where the plugs 50 are received in a receptacle 54 in the base 32.

FIG. 2A shows the body 34 in isolation without the base. As discussed, the body 34 can include the bottom surface 42 and the mechanical features 48A. As with FIG. 2, the mechanical features 48A can comprise the plugs 50 with features 52A. Each plug 50 can extend away from the body 34 and can be attached to the body 34 at the bottom surface 42.

FIG. 2B illustrates the positioning of features 52A and 52B in further detail. As shown in FIG. 2B, the plugs 50 can be received in the receptacle 54. Each feature 52A can comprise a circumferential projection (lip) on the plug 50. Similarly, feature 52B can comprise a generally circumferentially extending surface in receptacle 54. Thus, receptacle 54 can comprise a counter-bore in some instances. Feature 52B can act as a shoulder to retain the body 34 from axial movement relative to the base 32. Although not illustrated in the example of FIG. 2B, the base 32 can be provided with detents or other features along a circumference of the receptacle 54 or on the surface 42 that can arrest rotational movement of the body 34 relative to the base 32. Further examples of mechanical features, including, but not limited to, a fastener, a hook, detents, an adhesive, and combinations thereof can be utilized. In some instances, mechanical features 48A and 48B (FIG. 2) may not entirely fix the base 32 to the body 34 but can allow for some degree of movement if desired. For example, it may be desirable to allow for rotation of the body 34 relative to the base 32 in some instances.

In an example, the base 32 can be formed of a metal or metal alloy having a porous structure, such as a porous metal, that can facilitate bone ingrowth (e.g., act as a fixation aid for implant 30).

The enlargement of FIG. 2 illustrates such a porous structure 58. The porous metal structure 58 can include a plurality of ligaments 60 defining a plurality of highly interconnected, three-dimensional open spaces or pores 62 therebetween. The porous metal structure can incorporate one or more of a variety of biocompatible metals. Such structures are particularly suited for contacting bone and soft tissue, and in this regard, can be useful as a bone substitute and as cell and tissue receptive material, for example, by allowing tissue to grow into the porous structure over time to enhance fixation (e.g., osseointegration) between the structure and surrounding bodily structures. According to certain examples of the present disclosure, an open porous metal structure may have a porosity as low as 55%, 65%, or 75% or as high as 80%, 85%, or 90%, or within any range defined between any pair of the foregoing values. An example of an open porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other biocompatible metals may also be used in the formation of a highly porous metal structure such as titanium, a titanium alloy, cobalt chromium, cobalt chromium molybdenum, tantalum, a tantalum alloy, niobium, non-alloyed combination of tantalum or niobium with another metal, or alloys of tantalum and niobium with one another or with other metals. It is also within the scope of the present disclosure for a porous metal structure to be in the form of a fiber metal pad or a sintered metal layer, such as a Cancellous-Structured Titanium™ (CSTi™) layer. CSTi™ porous layers are manufactured by Zimmer, Inc., of Warsaw, Ind. Cancellous-Structured Titanium™ and CSTi™ are trademarks of Zimmer, Inc.

Generally, a porous metal structure will include a large plurality of metallic ligaments defining open voids (e.g., pores) or channels therebetween. The open spaces between the ligaments form a matrix of continuous channels having few or no dead ends, such that growth of soft tissue and/or bone through open porous metal is substantially uninhibited. Thus, the open porous metal may provide a lightweight, strong porous structure which is substantially uniform and consistent in composition, and provides a matrix (e.g., closely resembling the structure of natural cancellous bone) into which soft tissue and bone may grow to provide fixation of the implant to surrounding bodily structures. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced fixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the porous structure.

An open porous metal structure may also be fabricated such that it comprises a variety of densities in order to selectively tailor the structure for particular orthopedic applications. In particular, as discussed in the above-incorporated U.S. Pat. No. 5,282,861, an open porous metal structure may be fabricated to virtually any desired density, porosity, and pore size (e.g., pore diameter), and can thus be matched with the surrounding natural tissue (e.g., bone) in order to provide an improved matrix for tissue ingrowth and mineralization. According to certain examples, open porous metal structures may be fabricated to have a substantially uniform porosity, density, and/or void (pore) size throughout, or to comprise at least one of pore size, porosity, and/or density being varied within the structure. For example, an open porous metal structure may have a different pore size and/or porosity at different regions, layers, and surfaces of the structure. The ability to selectively tailor the structural properties of the open porous metal, for example, enables tailoring of the structure for distributing stress loads throughout the surrounding tissue and promoting specific tissue ingrowth within the open porous metal.

In other examples, an open porous metal structure may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another example of an open porous metal structure may comprise a metal substrate combined with a Ti-6Al-4V powder and a ceramic material, which is sintered under heat and pressure. The ceramic particles may thereafter be removed leaving voids, or pores, in the substrate. An open porous metal structure may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another example of an open porous metal structure may comprise a porous metal substrate having particles, comprising altered geometries, which are sintered to a plurality of outer layers of the metal substrate. Additionally, an open porous metal structure may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam. In yet further examples, additive processes may be utilized to construct the porous metal structure. In yet further examples, the porous structure can be created via additive process and can be subsequently CVD coated as described previously.

Because the base 32 can be formed of a porous metal structure, like the above-described porous tantalum, the base 32 can promote bone ingrowth, and can facilitate fixation of the base 32, and ultimately, the body 34 relative to bone and/or cartilage.

The body 34 can comprise a second porous material that differs from the porous metal material of the base 32. The porous material of body 34 can encourage cartilage ingrowth into the body 34 utilizing a ligament/void structure similar to the structure described in reference to the base 32. The porous material of the body 34 can comprise at least one of a polymeric material and a coral, for example, and can mimic the viscoelastic behavior of cartilage, in some instances. In cases where the body 34 comprises the polymeric material, the polymeric material can comprise a biocompatible polymer such as polycaprolactone, poly(lactic acid), poly(glycolic acid), copolymers of lactic acid and glycolic acid, poly(ethylene glycol), and combinations thereof.

The body 34 can be formed by extrusion, additive processing, or injection molding, for example, and can have a plurality of open pores on the surface that are interconnected to a network of interconnected pores in the interior thereof. The average porosity of the second material can range between about 40% to about 99% of the total volume of the second material. In some instances, the porosity may include pores with a diameter ranging between about 10 μm to about 1000 μm although radial and axial distributions of pore size and porosity can be varied as desired. In further instances, the porosity of the body 34 can be configured to substantially match the porosity and/or orientation of adjacent structures such as cartilage.

Figure 3:
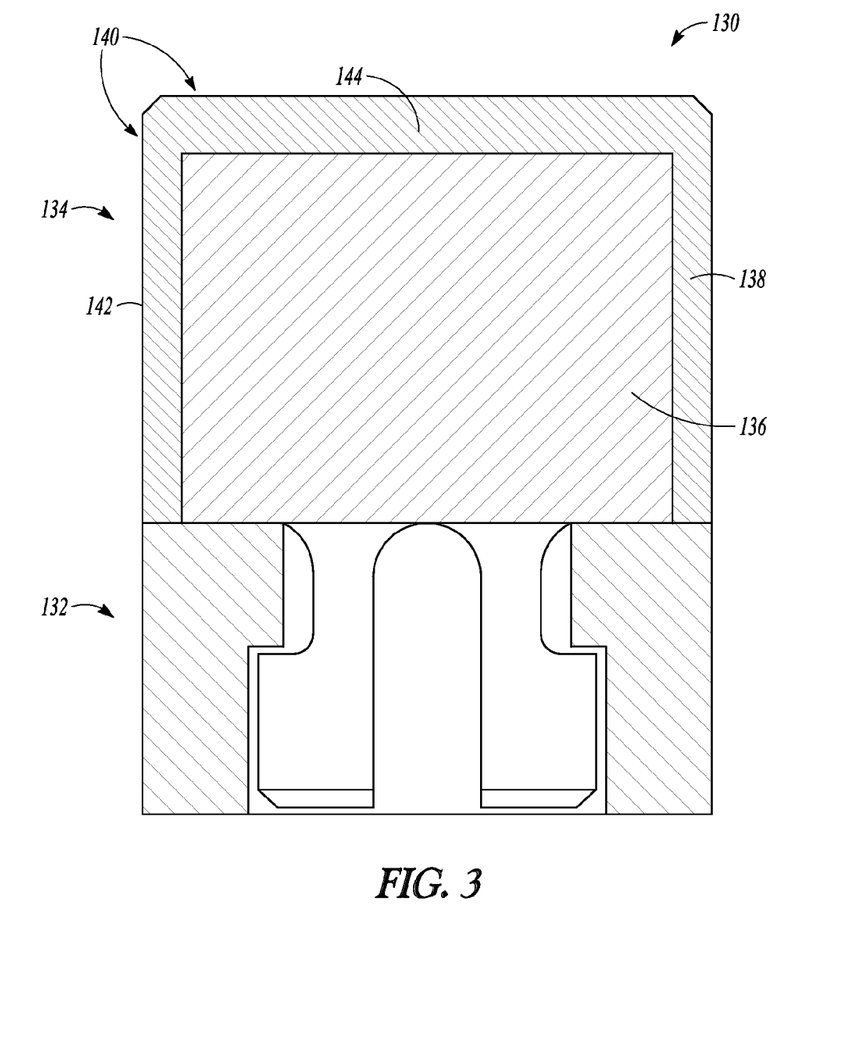
FIG. 3 is a cross-section of an implant including a body having a core and a shell, according to an example of the present application.

FIG. 3 illustrates a cross-section of another example of an implant 130. The implant 130 can include a base 132 and a body 134. The base 132 and the body 134 can be coupled together using the features previously described in reference to FIGS. 2-2B. The base 132 can be constructed in a manner similar to the base 32 (FIGS. 2 and 2B). However, the body 134 can comprise a different construction than that of the body 34 (FIGS. 2-2B).

According to the example of FIG. 3, the body 134 can comprise a core 136 and an outer shell 138. The core 136 can have a first porosity while the outer shell 138 can have a second porosity that differs from the first porosity. The core 136 and outer shell 138 can be formed of one of a polymeric material and/or a coral, for example. Thus, the core 136 and outer shell 138 can comprise the biocompatible polymeric materials previously discussed with reference to FIGS. 2-2B. The core 136 can be constructed from the same material as the outer shell 138 or different material(s) as desired.

The outer shell 138 can surround as least a portion of the core 136. In some instances, the second porosity of the outer shell 138 can be substantially similar to a porosity of adjacent cartilage. Additionally, the first porosity of the core 136 can be higher than the second porosity of the outer shell 138. Thus, the density of the core 136 can be lower than the density of the outer shell 138. The average porosity of both the core 136 and the outer shell 138 can range between about 60% to about 95% of the total volume of the body 134. In some instances, the porosity may include pores with a diameter ranging between about 10 μm to about 1000 μm although radial and axial distributions of pore size and porosity can varied as desired.

As illustrated in the example of FIG. 3, the core 136 can be coupled to the base 132. Thus, some of the coupling features previously discussed with reference to FIGS. 2-2B can be formed in or are part of core 136. The outer shell 138 can have a side portion 140 that forms side surface 142 and a top portion 144. The side portion 140 can be adapted to interface with adjacent cartilage. The top portion 144 of the outer shell 138 can surround a top portion of the core 136 that opposes and is spaced from the base 132. The top portion 144 can be adapted to interface with adjacent cartilage and can mimic the viscoelastic behavior of cartilage for uniformity, in some instances. According to some examples, the top portion 144 can be adapted to have a non-porous surface to aid in supporting and distributing dynamic loads of the joint.

Figure 4:
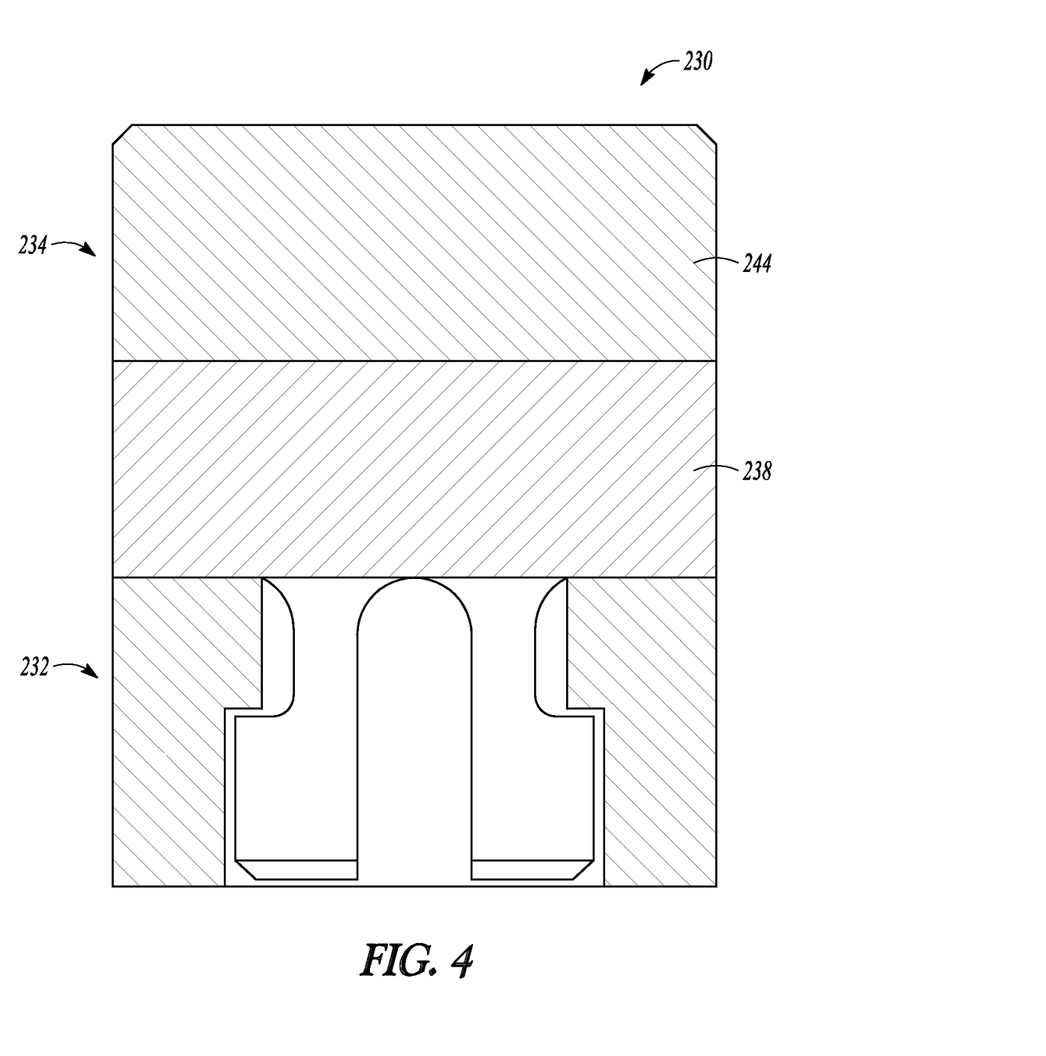
FIG. 4 is a cross-section of an implant including a body having two different porous parts, according to an example of the present application.

FIG. 4 illustrates another example of an implant 230. According to the example, the implant 230 can include a base 232 and a body 234. The body 234 can comprise a first portion 238 and a second portion 244. According to one example, the first portion 238 can include a first porosity that differs from a second porosity of the second portion 244. According to further examples, the first portion 238 can be comprised of a porous material such as previously discussed but the second portion 244 can be solid.

Figure 5:
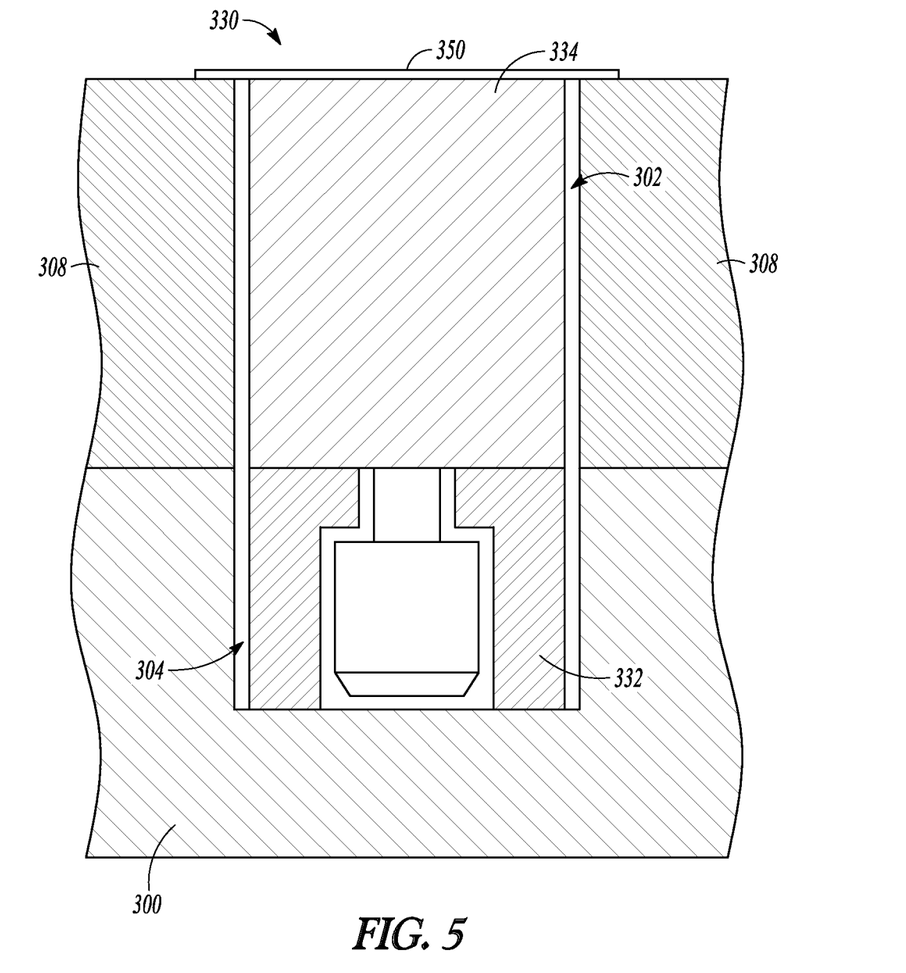
FIG. 5 is a partial cross-sectional view of an implant inserted in a bone of a joint to fill a cartilage void, according to an example of the present application.

FIG. 5 illustrates a schematic cross-sectional view of an implant 330 similar to implant 30 (FIGS. 2-2B) inserted in a bone 200 of a joint to fill a cartilage void 302. According to some examples, the implant 330 can include a plate 350 or similar solid object disposed along a top portion and across the cartilage void 302. The plate 350 can be adapted to be non-porous to aid in supporting and distributing dynamic loads of the joint.

According to the illustrated example, a physician can create an aperture 304 in the bone 300 underlying the cartilage void 302. The aperture 304 can be created with surgical instruments such as a drill that can remove at least a portion of the bone 300 that can be exposed by the cartilage void 302 to a desired axial depth to create the aperture 304 within the bone 300. The implant 330 can then be inserted into the aperture 304. The aperture 304 and implant 330 can be configured such that a base 332 of the implant 330 can be disposed adjacent the bone 300 while a body 334 of the implant 330 can be disposed adjacent cartilage 308. More specifically, the axial height (depth) of the aperture 304 and/or the base 332 can be configured to substantially match as illustrated in FIG. 5, such that the base 332 terminates at a similar height as bone 300. Further, the body 334 can be configured to have substantially a same axial height (thickness) as the cartilage 308 as illustrated in FIG. 5. Thus, the implant 330 (specifically, the body 334) can be used as a plug to fill the cartilage void 302, thereby allowing the body to interface with surrounding cartilage 308 and act as a cartilage scaffold to promote cartilage ingrowth. As discussed, fusion of the bone 300 into the base 332 can cause fixation of the implant 330 including the body 334, which can facilitate cartilage ingrowth into the body 334. Although aperture 304 is illustrated as having a similar diameter as cartilage void 302 in FIG. 5, in some cases the two may differ. Similarly, although the base 332 is illustrated as terminating at substantially the same axial height as the bone 300 in FIG. 5, in some instances the two may terminate at a different axial height. According to further examples, since the cartilage and subchondrial bone do not form a distinct boundary, the height of one or both of the base 332 and body 334 the might be designed to always be above or below the bone/cartilage transition zone.

According to an example of the present application, a method of treating a cartilage void within a patient is disclosed. The method can remove at least a portion of bone underlying the cartilage void to a desired depth to create an aperture within the bone. Additionally, the method can position an implant having a base comprising a porous metal material and a body comprising a second porous material within the aperture such that the base is disposed adjacent the bone and the body is disposed adjacent cartilage of the patient. In some instances, the positioning of the implant can configure the body as a cartilage scaffold and the base as a bone scaffold. In some cases, the porosity of the porous metal material can be between 55% and 90%. The porous metal material can comprise a tantalum or tantalum alloy. The second porous material can differ from the porous metal material and can comprise at least one of a polymeric material and a coral.

According to another example of the present application, an orthopedic implant is disclosed. The implant can include a base and a body. The base can comprise a porous metal material configured to encourage bone ingrowth into the base. The body can be coupled to the base and can comprise a second material that differs from the porous metal material of the base. The body can be configured to encourage cartilage ingrowth into the body. In some instances, the porosity of the porous metal material can be between 55% and 90%. The second material can be a porous material that comprises at least one of a polymeric material and a coral. The polymeric material can comprise a biocompatible polymer of at least one of polycaprolactone, poly(lactic acid), poly(glycolic acid), copolymers of lactic acid and glycolic acid, poly(ethylene glycol), and combinations thereof. The body can be coupled to the base by one or more mechanical features that can include at least one of a fastener, a hook, a detent, a feature, a plug, a male/female connection, an adhesive, and combinations thereof. The body can comprise a core having a first porosity and an outer shell surrounding as least a portion of the core. The outer shell can have a second porosity that differs from the first porosity. The second porosity of the outer shell can be substantially similar to a porosity of cartilage. The first porosity of the core can be higher than the second porosity of the outer shell. The core can be coupled to the base and the shell can surround at least a portion of the core that opposes and is spaced from the base. The base can comprise a tantalum or tantalum alloy with the porosity and adaptations previously described in reference to previous examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An orthopedic implant configured to treat a cartilage void in a patient, comprising:
   a base implantable into bone of the patient and comprising a porous metal material configured to encourage bone ingrowth into the base; and
   a body insertable into the cartilage void, coupled to the base and comprising a second material that differs from the porous metal material of the base, wherein the body is configured to encourage cartilage ingrowth into the body;
   wherein the body and the base have one or more mechanical features, and wherein the one or more mechanical features include a receptacle at least partially defined by a proximal part of the base, the receptacle configured for receiving a male connection portion extending from a distal part of the body therein to couple the base and the body, and wherein the one or more mechanical features of the body and the base are configured to allow for some degree of movement or rotation of the body relative to the base after assembly and prior to bone and cartilage ingrowth.

2. The implant of claim 1, wherein the porosity of the porous metal material is between 55% and 90%.

3. The implant of claim 1, wherein the second material is a porous material that comprises at least one of a polymeric material and a coral.

4. The implant of claim 3, wherein the polymeric material comprises a biocompatible polymer that includes at least one of polycaprolactone, poly(lactic acid), poly(glycolic acid), copolymers of lactic acid and glycolic acid, poly(ethylene glycol), and combinations thereof.

5. The implant of claim 1, wherein the porous metal material comprises a tantalum or tantalum alloy.

6. The implant of claim 1, wherein the receptacle comprises a counter-bore.

7. The implant of claim 1, wherein the one or more mechanical features of the base comprises a circumferentially extending surface that defines an interior portion of the receptacle.

8. The implant of claim 7, wherein the circumferentially extending surface comprises a shoulder that is configured to retain the body from axial movement relative to the base.

9. The implant of claim 1, wherein the one or more mechanical features of the body comprises a plug.

10. An orthopedic implant configured to treat a cartilage void in a patient, comprising:
    a base implantable into bone of the patient and comprising a porous metal material having a porosity between 55% and 90% configured to encourage bone ingrowth into the base to facilitate attachment of the base to bone; and
    a body insertable into the cartilage void and comprising a polymeric material configured to encourage cartilage ingrowth into the body;
    wherein the body and the base have one or more mechanical features, and wherein the one or more mechanical features include a receptacle at least partially defined by a proximal part of the base, the receptacle configured for receiving a plug extending from a distal part of the body therein to couple the base and the body, and wherein the one or more mechanical features of the body and the base are configured to allow for some degree of movement or rotation of the body relative to the base after assembly and prior to bone and cartilage ingrowth.

11. The implant of claim 10, wherein the polymeric material comprises a biocompatible polymer that includes at least one of polycaprolactone, poly(lactic acid), poly(glycolic acid), copolymers of lactic acid and glycolic acid, poly(ethylene glycol), and combinations thereof.

12. The implant of claim 10, wherein the porous metal material comprises a tantalum or tantalum alloy.

13. The implant of claim 10, wherein the receptacle comprises a counterbore.

14. The implant of claim 10, wherein the one or more mechanical features of the base comprises a circumferentially extending surface that defines an interior portion of the receptacle.

15. The implant of claim 14, wherein the circumferentially extending surface comprises a shoulder that is configured to retain the body from axial movement relative to the base.

* * * * *